US006652886B2

(12) United States Patent
Ahn et al.

(10) Patent No.: US 6,652,886 B2
(45) Date of Patent: Nov. 25, 2003

(54) BIODEGRADABLE CATIONIC COPOLYMERS OF POLY (ALKYLENIMINE) AND POLY (ETHYLENE GLYCOL) FOR THE DELIVERY OF BIOACTIVE AGENTS

(75) Inventors: Cheol Hee Ahn, Salt Lake City, UT (US); Sung Wan Kim, Salt Lake City, UT (US)

(73) Assignee: Expression Genetics, Sandy, UT (US)

( * ) Notice: Subject to any disclaimer, the term of this patent is extended or adjusted under 35 U.S.C. 154(b) by 0 days.

(21) Appl. No.: 09/785,525

(22) Filed: Feb. 16, 2001

(65) Prior Publication Data

US 2002/0141965 A1 Oct. 3, 2002

(51) Int. Cl.[7] .................................................. A61K 9/50
(52) U.S. Cl. ........................ 424/501; 424/489; 424/499; 424/484; 424/488; 424/422; 424/423; 424/426; 514/772.1
(58) Field of Search ................. 424/426, 422, 424/484, 423, 486, 488, 489, 499, 501; 514/772.1

(56) References Cited

U.S. PATENT DOCUMENTS

| | | | | |
|---|---|---|---|---|
| 4,187,256 | A | | 2/1980 | Jones et al. ................. 525/471 |
| 5,459,184 | A | * | 10/1995 | Bunnelle et al. ............. 524/221 |
| 5,516,852 | A | | 5/1996 | Kuo et al. .................... 525/340 |
| 5,629,184 | A | | 5/1997 | Goldenberg et al. ...... 435/172.3 |
| 5,679,559 | A | | 10/1997 | Kim et al. ................. 435/172.3 |
| 5,709,854 | A | * | 1/1998 | Griffith-Cima et al. ..... 424/93.7 |
| 5,948,878 | A | | 9/1999 | Burgess et al. .............. 528/272 |
| 6,013,240 | A | | 1/2000 | Behr et al. .................. 424/1.21 |
| 6,080,728 | A | | 6/2000 | Mixson ......................... 514/44 |
| 6,130,075 | A | * | 10/2000 | Planas et al. ................ 435/139 |
| 6,274,175 | B1 | * | 8/2001 | Gombotz et al. ............. 424/501 |

FOREIGN PATENT DOCUMENTS

| WO | WO 98/00556 | 1/1998 |
|---|---|---|
| WO | WO 98/19710 | 5/1998 |

OTHER PUBLICATIONS

R. Langer, New Methods of Drug Delivery; 249 Science 1527–1533 (1990).
B Jeong Biodegradable Block Copolymers as Injectable Drug–Delivery Systems, 388 Nature 860–862 (1997).
J. Cherng, Effect of Size and Serum Proteins on Transfection Efficiency of Poly ((2–Dimethylamino)Ethyl Methacrylate)–Plasmid Nanoparticles; Pharmaceutical Research vol. 13, No. 7, 1966.
A Maruyama, Nanoparticle DNA Carrier with Poly(L–Lysine) Grafted Polysaccharide Copolymer and Poly(D,L–Lactic Acid);Bioconjugate Chem. 1997, 8, 735–742.
D. Sgouras, Methods for the Evaluation of Biocompatibility of Soluble Synthetic Polymers Which Have Potential for Biomedical Use: 1—Use of the Tetrazolium–Based Colorimetric Assay (MTT) as a Preliminary Screen for Evaluation of In Vitro Cytotoxicity, J Mater Sci in Medicine 1 (1990) 61–68.

(List continued on next page.)

Primary Examiner—Thurman K. Page
Assistant Examiner—Liliana Di Nola-Baron
(74) Attorney, Agent, or Firm—Thorpe North & Western, LLP

(57) ABSTRACT

A biodegradable, novel cationic coopolymer comprising a a poly(alkylenimine)(PAI), a hydrophilic polymer, and a biodegradable linker, wherein the biodegradable linker covalently links the PAI and the hydrophilic polymer. The biodegradable cationic copolymers in the present invention can be used in drug delivery and are especially useful for delivery of a nucleic acid or any anionic bioactive agent to various organs and tissues after local or systemic administration.

27 Claims, 4 Drawing Sheets

OTHER PUBLICATIONS

WT Godbey, Poly(Ethylenimine)–Mediated Transfection: A New Paradigm For Gene Delivery, 51 J. Biomed Mater. Res. 321 (2000).

WT Godbey, Poly(Ethylenimine) and its Role in Gene Delivery, J of Controlled Release 60 (1999) 149–160.

D Dunlap, Nanoscopic Structure of DNA Condensed For Gene Delivery, Nucleic Acids Res, 1997, vol. 25, No. 15, 3095–3101.

O Boussif, A Versatile Vector For Gene and Oligonucleotide Transfer Into Cells In Culture And In Vivo: Polyethylenimine, Proc Natl Acad Sci, vol. 92, pp 7297–7301, 1995.

S. Brunner, Cell Cycle Dependence of Gene Transfer by Lipoplex, Polyplex and Recombinant Adenovirus, Gene Therapy 7, 401–407 (2000).

D. Fischer, A Novel Non–Viral Vector for DNA Delivery Based On Low Molecular Weight, Branched Polyethylenimine: Effect of Molecular Weight on Transfection Effi ciency and Cytotoxicity, Pharmaceutical Res. vol. 16, No. 8, 1999.

WT Godbey, Size Matters: Molecular Weight Affects the Efficiency of Poly(Ethylenimine) As A Gene Delivery Vehicle, Biomed Mater Res. 45, 268–245 (1999).

AV Kabanov, DNA Complexes With Polycations For The Delivery of Genetic Material Into Cells, Bioconjugate Chem. 1995, 6, 7–20.

Y. Akiyama, Synthesis of Poly(Ethylene Glycol)–Block – Poly(Ethylenimine) Possessing an Acetal Group at the Peg End, Macromolecules 2000, 33, 5841–5845.

S. Vinogradov, Self–Assembly of Polyamine–Poly(Ethylene Glycol) Copolymers With Phosphorothioate Oligonucleotides, Bioconjugate Chem. 1998, 9, 805–812.

* cited by examiner

BIODEGRADABLE CATIONIC COPOLYMERS OF POLY (ALKYLENIMINE) AND POLY (ETHYLENE GLYCOL) FOR THE DELIVERY OF BIOACTIVE AGENTS

FIELD OF THE INVENTION

This invention relates to delivery of a bioactive agent. More particularly, the invention relates to a composition and method for delivering bioactive agents, such as DNA, RNA, oligonucleotides, proteins, peptides, and drugs, by facilitating their transmembrane transport or by enhancing their adhesion to biological surfaces. It relates particularly to a biodegradable cationic copolymer of a poly(alkylenimine) (PAI) and a hydrophilic polymer wherein the PAI and the hydrophilic polymer are covalently linked by a biodegradable linkage. The cationic copolymers of the present invention can be used in drug delivery and are especially useful for delivery of nucleic acids or any anionic bioactive agents.

BACKGROUND OF THE INVENTION

Biodegradable polymers are gaining attention as drug delivery systems. R. Langer, New Methods of Drug delivery, 249 Science 1527–1533 (1990); B. Jeong et al., Biodegradable Block Copolymers as Injectable Drug-delivery Systems, 388 Nature 860–862 (1997). Delivering bioactive agents from a biodegradable delivery system is highly desirable because the need for a surgical procedure to remove the delivery system is avoided. Controlled release of bioactive agents can reduce the required frequency of administration by maintaining the concentration of the therapeutic agent at desired levels. One important means of maintaining the proper concentration is by controlling the degradation rate of the biodegradable drug delivery system.

Gene therapy is generally considered as a promising approach, not only for the treatment of diseases with genetic defects, but also in the development of strategies for treatment and prevention of chronic diseases such as cancer, cardiovascular disease and rheumatoid arthritis. However, nucleic acids, as well as other polyanionic substances, are rapidly degraded by nucleases and exhibit poor cellular uptake when delivered in aqueous solutions. Since early efforts to identify methods for delivery of nucleic acids in tissue culture cells in the mid 1950's, steady progress has been made towards improving delivery of functional DNA, RNA, and antisense oligonucleotides in vitro and in vivo.

The gene carriers used so far include viral systems (retroviruses, adenoviruses, adeno-associated viruses, or herpes simplex viruses) or nonviral systems (liposomes, polymers, peptides, calcium phosphate precipitation and electroporation). Viral vectors have been shown to have high transfection efficiency when compared to non-viral vectors, but due to several drawbacks, such as targeting only dividing cells, random DNA insertion, their low capacity for carrying large sized therapeutic genes, risk of replication, and possible host immune reaction, their use in vivo is severely limited.

An ideal transfection reagent should exhibit a high level of transfection activity without needing any mechanical or physical manipulation of the cells or tissues. The reagent should be non-toxic, or minimally toxic, at the effective dose. It should also be biodegradable in order to avoid any long-term adverse side-effects on the treated cells. When gene carriers are used for delivery of nucleic acids in vivo, it is essential that the gene carriers themselves be nontoxic and that they degrade into non-toxic products. To minimize the toxicity of the intact gene carrier and its degradation products, the design of gene carriers needs to be based on naturally occurring metabolites.

Because of their sub-cellular size, nanoparticles are hypothesized to enhance interfacial cellular uptake, thus achieving in a true sense a local pharmacological drug effect. It is also hypothesized that there would be enhanced cellular uptake of drugs contained in nanoparticles (due to endocytosis) compared to the uptake of the corresponding free drug. Nanoparticles have been investigated as drug carrier systems for tumor localization of therapeutic agents in cancer therapy, for intracellular targeting (antiviral or antibacterial agents), for targeting to the reticuloendothelial system (parasitic infections), as an immunological adjuvant (by oral and subcutaneous routes), for ocular delivery with sustained drug action, and for prolonged systemic drug therapy.

As compared to viral gene carriers, there are several advantages to the use of non-viral based gene therapies, including their relative safety and low cost of manufacture. Non-viral gene delivery systems such as cationic polymers or synthetic gene carriers, e.g. poly-L-lysine (PLL), are being widely sought as alternatives and investigated intensively to circumvent some of the problems encountered with use of viral vectors. J. Cheng et al., Effect of Size and Serum Proteins on Transfection Efficiency of Poly((2-dimethylamino)ethyl methacrylate)-plasmid nanoparticles, 13 Pharm. Res. 1038–1042 (1996). There are several polymeric materials currently being investigated for use as gene carriers, of which poly-L-lysine (PLL) is the most popular, but few of them are biodegradable. Biodegradable polymers, such as polylactic/glycolic acid(negatively charged), and polylactide/glycolide(neutral) have been used as gene carriers in the form of non-soluble particulates. Amarucyama et al, Nanoparticle DNA Carrier with PLL Grafted Polysallanide Copolymer and Polylactic Acid, 8 Bioconjugate, 735–739(1997). In general, cationic polymers are known to be toxic and the PLL backbone is barely degraded under physiological conditions. It remains in cells and tissues and causes an undesirably high toxicity. A. Segouras & R. Dunlan, Methods for Evaluation of Biocompatibility of Synthetic Polymers, 1 J.Mater.Sci in Medicine, 61–68 (1990).

PAIs such as poly(ethylenimine) (PEI) and polyspermine have been known as efficient gene carriers with high cationic charge potentials. Branched PEI consists of approximately 25, 50 and 25% of primary, secondary and tertiary amines and is able to condense and deliver DNA in vitro and in vivo, W. T. Godbey et al., 51 J. Biomed. Mater. Res. 321 (2000); W. T. Godbey et al., 60 J. Contr. Rel. 149 (1999); D. D. Dunlap et al., 25 Nucleic Acids Research 3095 (1997); O. Boussif et al., 92 Proc. Nat l Acad. Sci. USA 7297 (1995). Primary amines of PEI are reported to participate in forming complexes with DNA by ionic interaction with phosphate groups, while the secondary and tertiary amines cause a substantial endosomal disruption after endocytosis due to their buffering effect which contributes to the high transfection efficiency of PEI. The high transfection efficiency of PEI, along with its cytotoxicity, strongly depends on its molecular weight. It is generally believed that PEI with a molecular weight higher than 25 K displays a high transfection efficiency and toxicity, while PEI with molecular weight less than 1.8 K shows almost no transfection, but is less toxic, S. Brunner et al., 7 Gene Ther. 401 (2000); D. Fischer et al., 16 Pharm. Res. 1273 (1999); W. T. Godbey et al., 45 J. Biomed. Mater. Res. 268 (1999). In addition, just like most cationic polymers, PEI has drawbacks since complexes of PEI and DNA are often poorly soluble under physiological conditions, A. V. Kabanov et al., 6 Bioconjugate Chem. 7 (1995).

Di-block and graft copolymers of PEI and PEG have been synthesized and investigated by several research groups, Y. Akiyama et al., 33 Macromolecules 5841 (2000); S. V. Vinogradov et al., 9 Bioconjugate Chem. 805 (1998). Although copolymers of high molecular weight PEI and PEG exhibit considerable transfection efficiency, with the employment of high molecular weight PEI, cytotoxicity still remains as a problem. In addition, none of the existing copolymers of PEI and PEG are biodegradable.

In view of the foregoing, development of a gene carrier for gene therapy and drug delivery that is non-toxic, biodegradable, and capable of forming nanoparticles, or transfection complexes will be appreciated and desired. The novel gene carrier of the present invention comprises a novel cationic copolymer of a poly(alkylenimine) (PAI) and a hydrophilic polymer, wherein the PAI and the hydrophilic polymer are covalently linked by a biodegradable linkage. The biodegradable cationic copolymer of the present invention is useful for drug delivery, especially for delivery of nucleic acids, other anionic bioactive molecules, or both, and is readily susceptible to metabolic degradation after incorporation into the cell.

BRIEF SUMMARY OF THE INVENTION

The present invention provides a biodegradable cationic copolymer, having reduced in vivo and in vitro toxicity, useful for delivery of drugs or other bioactive agents to an individual in need thereof.

The present invention also provides biodegradable water soluble cationic copolymers that are able to condense DNA and form stable complexes with DNA under physiological conditions.

The present invention further provides an efficient non-viral polymer-based water-soluble system for delivery of DNA or RNA to a target cell.

The present invention further provides an efficient polymer-based water-insoluble system for delivery of proteins or other bioactive agents.

The biodegradable cationic copolymer of the present invention comprises a biodegradable cationic copolymer of a poly(alkylenimine) (PAI) and a hydrophilic polymer wherein the PAI and the hydrophilic polymer are covalently linked by a biodegradable linkage. Preferably, the hydrophilic polymer is a member selected from the group consisting of polyethylene glycol (PEG), poloxamers, poly(acrylic acid), poly(styrene sulfonate), carboxymethylcellulose, poly(vinyl alcohol), polyvinylpyrrolidone, alpha-substituted poly(oxyalkyl) glycols, poly(oxyalkyl) glycol copolymers and block copolymers, and activated derivatives thereof. More preferably, the hydrophilic polymer is a member selected from the group consisting of polyethylene glycol (PEG), poloxamers, poly(acrylic acid), poly(styrene sulfonate), carboxymethylcellulose, poly(vinyl alcohol) and polyvinylpyrrolidone. The most preferred hydrophilic polymer is polyethylene glycol (PEG). Preferably, the average molecular weight of the PAI is within a range of 600 to 100,000 Daltons and the average molecular weight of the hydrophilic polymer is within a range of 500 to 20,000 Daltons. The PAI is conjugated to the hydrophilic polymer by a biodegradable linkage which can be an ester, amide or urethane, depending on the required degradation rate. The molar ratio of the PAI to the hydrophilic polymer is preferably within a range of 0.1 to 2. Due to the multi-functionality of PAIs, the solubility in water of the synthesized copolymers can be controlled by the reaction conditions. A preferred cationic copolymer is a copolymer of a low molecular weight PAI and PEG, which exhibits negligible toxicity and high transfection efficiency.

Hydrophilic PEG is expected to reduce the toxicity of the copolymer, improve the poor solubility of the PAI and DNA complexes, and help to introduce biodegradable groups by reaction with the primary amines in the PAI. Considering the dependence of transfection efficiency and cytotoxicity on the molecular weight of the PAI, high transfection efficiency is expected from an increased molecular weight of the copolymer and low cytotoxicity from the degradation of the copolymer into minimally toxic low molecular weight PAIs.

The biodegradable copolymers can be synthesized by relatively simple and inexpensive methods. The biodegradable water soluble cationic copolymer is synthesized by reacting a branched or linear PAI with PEG, having difunctional groups, that produces biodegradable linkages with the primary amino groups in the PAI. Initial polymer concentrations of the reaction mixture, the number of functional groups in the PAI which is related to the initial molecular weight of the PAI, and the other reaction conditions should be carefully controlled to prevent possible cross-linking reactions. The molecular weight of the copolymer and the molar ratio of the PAI and PEG in the copolymer can be adjusted by changing the initial concentration of the PAI and the difunctional PEG. The biodegradable water insoluble copolymer can be synthesized using a method similar to that employed in making the water soluble copolymers except for the higher initial concentration of the reaction mixture and the higher molecular weight of the initial PAI.

The cationic copolymers of the present invention can spontaneously form discrete nanometer-sized particles with a nucleic acid, which can promote more efficient gene transfection into mammalian cells and show reduced cell toxicity. The copolymer of the present invention is readily susceptible to metabolic degradation after incorporation into animal cells. Moreover, the water soluble cationic copolymer can form an aqueous micellar solution which is particularly useful for systemic delivery of various bioactive agents such as DNA, proteins, hydrophobic or hydrophilic drugs. The water insoluble copolymer can form cationic nanoparticles which is particularly useful for local drug delivery. Therefore, the biocompatible and biodegradable cationic copolymer of this invention provides an improved gene carrier for use as a general reagent for transfection of mammalian cells, and for the in vivo application of gene therapy.

The present invention further provides transfection formulations, comprising a novel cationic copolymer complexed with a selected nucleic acid, in the proper charge ratio (positive charge of the copolymer/negative charge of the nucleic acid), that is optimally effective for both in vivo and in vitro transfection. Particularly, the weight ratio of DNA to the cationic copolymer is preferably within a range of 1:0.3 to 1:16.

This invention also provides for a method of transfecting a cell in vitro with biodegradable water soluble cationic copolymers and a selected plasmid DNA, comprising the steps of:

(a) providing a composition comprising a complex with an effective amount of positively charged cationic biodegradable polymer and plasmid DNA.

(b) Contacting the cell with an effective amount of the composition such that the cell internalizes the selected plasmid DNA; and (c) Culturing the cell with the internalized selected plasmid DNA under conditions favorable for the growth thereof.

DETAILED DESCRIPTION

Figure 1:
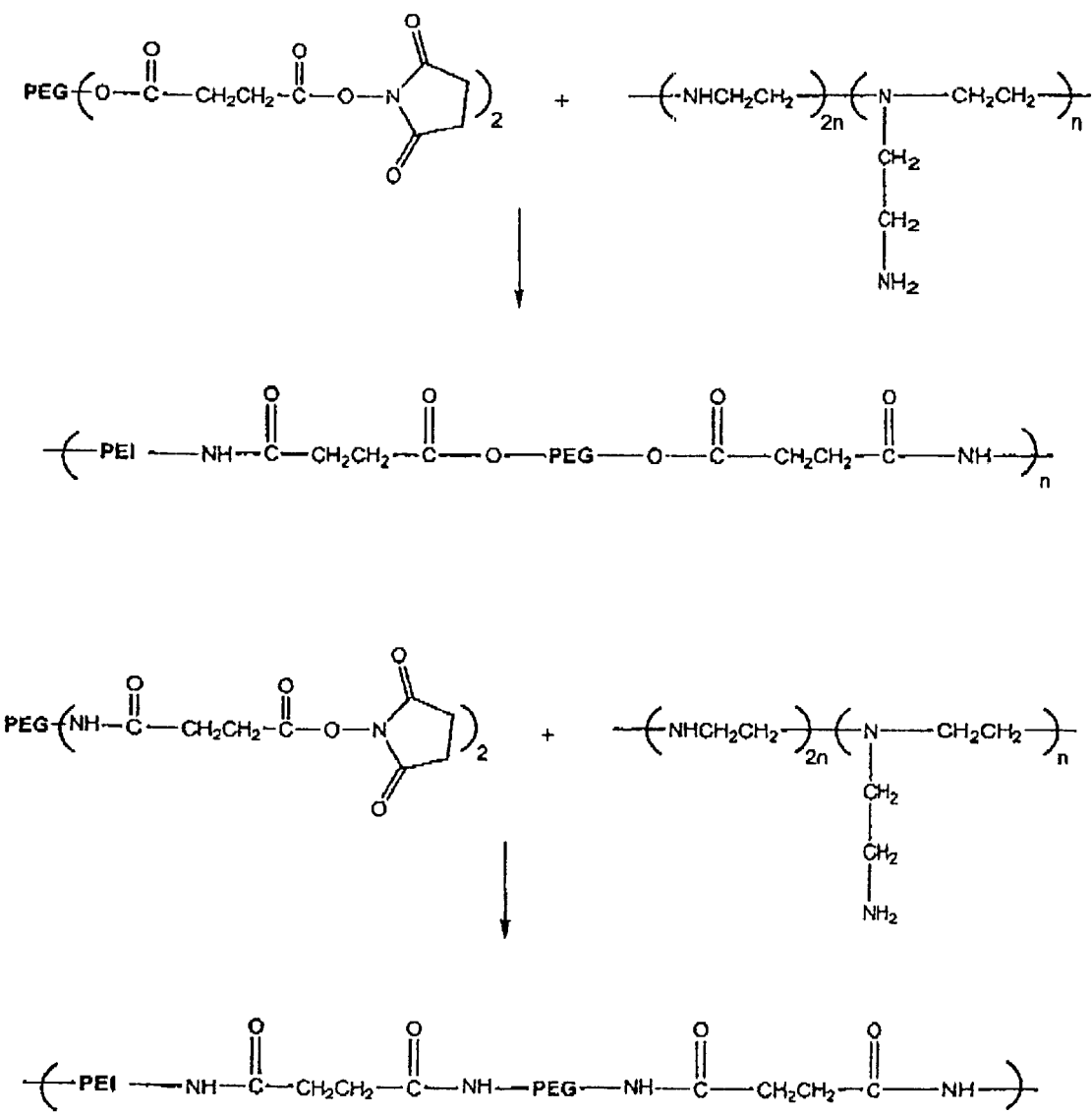
FIG. 1 illustrates a reaction scheme of the synthesis of biodegradable water soluble cationic copolymers from PAI and difunctional PEG.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof. It must be noted that, as used in this specification and the appended claims, the singular forms "a," "an," and "the" include plural referents unless the context clearly dictates otherwise. Thus, for example, reference to a polymer containing "sugar" includes reference to two or more of such sugars, reference to "ligand" includes reference to one or more of such ligands, and reference to "drug" includes reference to two or more of such drugs.

In describing and claiming the present invention, the following terminology will be used in accordance with the definitions set out below.

"Transfecting" or "transfection" shall mean transport of nucleic acids from the environment external to a cell to the internal cellular environment, with particular reference to the cytoplasm and/or cell nucleus. Without being bound by any particular theory, it is understood that nucleic acids may be delivered to cells either after being encapsulated within or adhering to one or more cationic lipid/nucleic acid complexes or entrained therewith. Particular transfecting instances deliver a nucleic acid to a cell nucleus. Nucleic acids include both DNA and RNA as well as synthetic congeners thereof. Such nucleic acids include missense, antisense, nonsense, as well as protein producing nucleotides, on and off and rate regulatory nucleotides that control protein, peptide, and nucleic acid production. In particular, but nonlimiting, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. These nucleic acids may be of human, animal, vegetable, bacterial, viral, and the like, origin. They may be obtained by any technique known to a person skilled in the art.

As used herein, the term "bioactive agent" or "drug" or any other similar term means any chemical or biological material or compound suitable for administration by the methods previously known in the art and/or by the methods taught in the present invention and that induce a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic.

This invention is not drawn to novel drugs or to new classes of bioactive agents per se. Rather it is drawn to biodegradable cationic copolymer compositions and methods of using such compositions for the delivery of genes or other bioactive agents that exist in the state of the art or that may later be established as active agents and that are suitable for delivery by the present invention. Such substances include broad classes of compounds normally delivered into the body. In general, this includes but is not limited to: nucleic acids, such as DNA, RNA, and oligonucleotides, antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium, calcium channel blockers, beta-blockers, alpha-blockers, and antiarrhythmics; antihypertensives; diuretics and antidiuretics; vasodilators including general, coronary, peripheral and cerebral; central nervous system stimulants; vasoconstrictors; cough and cold preparations, including decongestants; hormones such as estradiol and other steroids including corticosteroids; hypnotics; immunosuppressives; muscle relaxants; parasympatholytics; psychostimulants; sedatives; and tranquilizers. By the method of the present invention, drugs in all forms, e.g. ionized, nonionized, free base, acid addition salt, and the like may be delivered, as can drugs of either high or low molecular weight. The only limitation to the genus or species of bioactive agent to be delivered is that of functionality which can be readily determined by routine experimentation.

As used herein, the term "biodegradable" or "biodegradation" is defined as the conversion of materials into less complex intermediates or end products by solubilization hydrolysis, or by the action of biologically formed entities which can be enzymes and other products of the organism.

As used herein, "effective amount" means an amount of a nucleic acid or a bioactive agent that is sufficient to provide the desired local or systemic effect and performance at a reasonable risk/benefit ratio as would attend any medical treatment.

As used herein, "peptide", means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, "administering", and similar terms means delivering the composition to the individual being treated such that the composition is capable of being circulated systemically where the composition binds to a target cell and is taken up by endocytosis. Thus, the composition is preferably administered to the individual systemically, typically by subcutaneous, intramuscular, transdermal, intravenous, or intraperitoneal administration. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like.

Fundamental to the success of gene therapy is the development of gene delivery vehicles that are safe and efficacious after systemic administration. PAIs have been shown to be highly effective in gene transfer, which is dependent on their molecular weight and charge ratio. However, high molecular weight PAIs are sufficiently toxic to cells and tissues to render the use thereof unacceptable.

The present invention provides a biodegradable cationic copolymer of a poly(alkylenimine) (PAI) and a hydrophilic polymer wherein the PAI and the hydrophilic polymer are covalently linked by a biodegradable linkage. Preferably, the hydrophilic polymer is a member selected from the group consisting of polyethylene glycol (PEG), poloxamers, poly (acrylic acid), poly(styrene sulfonate), carboxymethylcellulose, poly(vinyl alcohol), polyvinylpyrrolidone, alpha-substituted poly(oxyalkyl) glycols, poly(oxyalkyl) glycol copolymers and block copolymers, and activated derivatives thereof. More preferably, the hydrophilic polymer is a member selected from the group consisting of polyethylene glycol (PEG), poloxamers, poly(acrylic acid), poly(styrene sulfonate), carboxymethylcellulose, poly(vinyl alcohol) and polyvinylpyrrolidone. The most preferred hydrophilic polymer is polyethylene glycol (PEG). Preferably, the average molecular weight of the PAI is within a range of 600 to 100,000 Daltons and the average molecular weight of the hydrophilic polymer is within a range of 500 to 20,000 Daltons. The PAI is conjugated to the hydrophilic polymer by a biodegradable linkage which can be an ester, amide or urethane, depending on the required degradation rate. The molar ratio of the PAI to the hydrophilic polymer is preferably within a range of 0.1:1 to 2:1. Primary, secondary and tertiary amines of PEI contained in the biodegradable copolymer of PAI and PEG provide sufficient positive charges for adequate DNA condensation.

The biodegradable water soluble cationic copolymer is synthesized by reacting a branched or linear PAI with PEG that has difunctional groups which produce biodegradable linkages with the primary amino groups in the PAI. The initial polymer concentrations of the reaction mixture, the number of functional groups in the PAI which is related to the initial molecular weight of the PAI, and other reaction conditions should be carefully controlled to prevent possible cross-linking reactions. The molecular weight of the copolymer and the molar ratio of the PAI and PEG in the copolymer can be adjusted by changing the initial concentration of the PAI and the difunctional PEG. The difunctional PEGs used in the present invention are the derivatives of PEG which bear electrophilic groups that are reactive towards the primary amino groups in the PAI. The chemical structure of the PAI in the present invention is as follows:

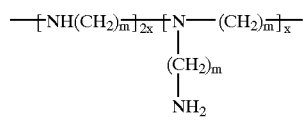

wherein m is an integer from 1 to 6 and x is an integer from 4 to 800. Due to the chemical structure of the PAI, which has more than two primary amino groups, the reaction between difunctional PEGs and the PAI generally results in a non-soluble cross-linked polymer. Therefore, careful control over the reaction conditions, such as the concentrations of the reactants, the reaction temperature, addition rate of difunctional PEG, and the molecular weight of the initial PAI, makes it possible to produce either biodegradable water soluble copolymers or biodegradable water insoluble copolymers. The synthetic scheme of the biodegradable cationic copolymers of the present invention can be illustrated as the following formula:

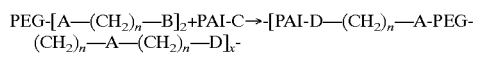

wherein n is an integer from 1 to 4; A is a member selected from the group consisting of ester, ether, sulfide, amide, and urethane; B is a member selected from the group consisting of H-hydroxysuccinimidyl ester and N-hydroxysuccinimidyl carbonate; C is a member selected from the group consisting of hydrogen, and —$(CH_2)_p NH_2$ wherein p is an integer from 1 to 6; and D is a member selected from the group consisting of amide and urethane.

In accordance with the present invention, the biodegradable linkage is a member selected from the group consisting of esters, amides and urethanes. The capability of selecting the biodegradable linkage between the PAI and the PEG of the cationic copolymer is very useful because it enables one to synthesize cationic copolymers displaying different degradation rates depending on the nature of the linkage group.

The molecular weight of the starting PAI in synthesizing the biodegradable cationic copolymer of the present invention can be varied from 600 to 100,000 Daltons and the molecular weight of the hydrophilic polymer can be varied from 500 to 20,000 Daltons. The biodegradable cationic copolymers suitable for the present invention have molecular weights in a range from 2,000 to 1,000,000 Daltons, depending on the molecular weight and mole ratio of the initial PAI and PEG.

Using $^1$H NMR with $CDCl_3$ as a solvent, molar ratios of [PAI]/[PEG] can be calculated by comparing the peak area from the ethylene group of PEG, around 3.65 ppm, to the alkylene group of the PAI, around 2.6 ppm. The molar ratio, [PAI]/[PEG], can be varied from 0.1 to 2. When a high molecular weight PAI is employed in the synthesis, difunctional PEG undergoes intramolecular reaction more easily with the excess amount of primary amino groups in the PAI, which results in a molar ratio of [PAI]/[PEG] of less than 1.

The biodegradable cationic copolymer of the present invention has amine group(s) which are electrostatically attracted to polyanionic compounds such as nucleic acids. The cationic copolymer of the present invention condenses DNA, for example, into compact structures. Upon administration, such complexes of these cationic copolymers and nucleic acids are internalized into cells through receptor mediated endocytosis. In addition, using a relatively low molecular weight PAI to form a copolymer of the PAI and PEI with a biodegradable linkage, reduces the potential cytotoxicity and increases the transfection efficiency of the copolymer.

The amine groups on the PAI can also be conjugated either directly to the amine groups or via spacer molecules, with targeting ligands. Preferably, only a portion of the available amine groups are coupled to the ligand such that the net charge of the copolymer is positive. The target ligands conjugated to the copolymer direct the copolymer-nucleic acid/drug complex to bind to specific target cells and penetrate into such cells(tumor cells, liver cells, heamatopoietic cells, and the like). The target ligands can also be an intraellular targeting element, enabling the transfer of the nucleic acid/drug to be guided towards certain favored cellular compartments (mitochondria, nucleus, and the like). In a preferred embodiment, the ligands can be sugar moieties coupled to the amino groups. Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid. The galactosyl unit of lactose provides a convenient targeting molecule for hepatocyte cells because of the high affinity and avidity of the galactose receptor on these cells.

Other types of targeting ligands that can be used include peptides such as antibodies or antibody fragments, cell receptors, growth factor receptors, cytokine receptors, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like.

An advantage of the present invention is that it provides a gene carrier wherein the particle size and charge density are easily controlled. Control of particle size is crucial for optimization of a gene delivery system because the particle size often governs the transfection efficiency, cytotoxicity, and tissue targeting in vivo. In general, in order to enable its effective penetration into tissue, the size of a gene delivery particle should not exceed the size of a virus. In the present invention, the particle size can be varied by using different ratios of the PAI to PEG and the initial molecular weight of the PAI and PEG which in turn determines the particle size of the-nucleic acid complex.

In a preferred embodiment of the invention, the particle sizes will range from about 80 to 200 nm depending on the cationic copolymer composition and the mixing ratio of the components. It is known that particles, nanospheres, and microspheres of different sizes, when injected, accumulate in different organs of the body depending on the size of the particles injected. For example, after systemic administration, particles of less than 150 nm diameter can pass through the sinusoidal fenestrations of the liver endothelium and become localized, in the spleen, bone marrow, and possibly tumor tissue. Intravenous, intra-arterial, or intraperitoneal injection of particles approximately 0.1 to 2.0 $\mu$m diameter leads to rapid clearance of the particles from the blood stream by macrophages of the reticuloendothelial system.

It is believed that the presently claimed composition is effective in delivering, by endocytosis, a selected nucleic acid into hepatocytes mediated by galactosyl receptors on the surface of the hepatocyte cells. Nucleic acid transfer to other cells can be carried out by matching a cell having a selected receptor thereof with a selected sugar. For example, the carbohydrate-conjugated cationic lipids of the present invention can be prepared from mannose for transfecting macrophages, from N-acetyllactosamine for transfecting T cells, and galactose for transfecting colon carcinoma cells.

By adjusting the molecular weight of the PAI and the molar ratio of the PAI to the PEG and/or other initial reaction conditions, the resultant copolymer can be either water soluble or water insoluble. For example, to obtain a water soluble copolymer of the present invention, the average molecular weight of the PAI is preferably within a range of 600 to 10,000 Daltons, and the molar ratio of the PAI to the PEG is preferably within a range of 1 to 2. To obtain a water insoluble copolymer of the present invention, the average molecular weight of the PAI is preferably within a range of 10,000? to 100,000 Daltons, and the molar ratio of the PAI to the hydrophilic polymer is preferably within a range of 0.1 to 1.

The water soluble cationic copolymers can be used as gene carriers which have high transfection efficiency and low toxicity. Such biodegradable cationic copolymers are also useful for the manufacture of sustained, continuous release injectable formulations of drugs. They can act as very efficient dispersing agents and can be administered by injection to give sustained release of drugs.

The water insoluble copolymers of the invention can be used to form cationic nanoparticles for delivery of protein drugs. The charge ratio (+/−) is preferably 7 to 16 for systemic delivery and 7 to 16 for local delivery. This ratio may be manipulated or varied by a person skilled in the art in accordance with the polymer used, the presence of an adjuvant, the nucleic acid, the target cell and the mode of the administration used.

Since cationic copolymers are known to be good for intracellular delivery of substances other than nucleic acids, the biodegradable cationic copolymers of PAIs and PEG can be used for the cellular delivery of substances other than nucleic acids, such as, for example, proteins and various pharmaceutical or bioactive agents. Examples of peptide and protein drugs include, but are not limited to LHRH analogues, desmopressin, oxytocin, neurotensin, acetylneurotensin, captopril, carbetocin, antocin II, octreotide, thyrotropin-releasing hormone(TRH), cyclosporine, enkephalins, insulin, calcitonin, interferons, GM-CSF, G-CSF, alpha-1 antitrpsin, alpha-a proteinase inhibito, dexoyribonuclease, growth hormone, growth factors, and erthropoietin.

The present invention therefore provides methods for treating various disease states, so long as the treatment involves transfer of material into cells. In particular, treating the following disease states is included within the scope of this invention: cancers, infectious diseases, inflammatory diseases and genetic hereditary diseases.

The biodegradable cationic copolymer of a PAI and a hydrophilic polymer, as described herein, exhibit improved cellular binding and uptake characteristics toward the bioactive agent to be delivered. As such, the present invention overcomes the problems associated with the use of high molecular weight PAIs, as set forth above. For example, the biodegradable cationic copolymer of the PAI and PEG is easily hydrolyzed or converted to a low molecular weight PAI and PEG in the body. The degraded low molecular weight PAI and PEG will easily be eliminated from the body. In addition, the degradation products are small, non-toxic molecules, that are subject to renal excretion and are inert during the period required for gene expression. Degradation is by simple hydrolytic and/or enzymatic reaction. Enzymatic degradation may be significant in certain organelles, such as lysosomes. It is particularly advantageous for the present invention that the degradation rate of the cationic copolymer can be controlled by choosing the biodegradable linkage between the PAI and PEG.

Furthermore, nanoparticles or transfection complexes can be formed from the cationic copolymer and nucleic acids or other negatively charged bioactive agents by simple mixing. Therefore, the cationic gene carrier of the present invention provides improved transfection efficiency and reduced cell toxicity.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE 1

This example illustrates the preparation of biodegradable cationic copolymers of PAI and PEG.

To a 250 ml flask, equipped with a magnetic stirrer, were added 50 ml anhydrous $CH_2Cl_2$, 0.1 ml anhydrous triethylamine and a predetermined amount of a PAI. After the PAI dissolved in the reaction solution, a predetermined amount of a difunctional PEG, dissolved in a 30 ml anhydrous $CH_2Cl_2$, was added dropwise over a 2 hour period of time. After additional stirring for 4 hours, the reaction mixture was filtered and condensed under reduced pressure. The condensed solution was precipitated into cold $Et_2O$ and the product was dried under vacuum overnight. The obtained polymer was then dissolved again in double distilled $H_2O$, centrifuged and filtered. The aqueous solution was freeze-dried for 2 days to give biodegradable cationic copolymers. Depending on the initial molecular weight of the PAI and PEG, the ratio of the PAI and PEG, and other reaction conditions, the synthesized cationic copolymer may be water soluble or water insoluble. Table 1 summarizes the reaction mixtures and the properties of the obtained copolymers.

TABLE 1

| Initial Molecular Weight | | Concentration (mol/L) | | Solubility in |
|---|---|---|---|---|
| PEI | PEG | PEI | PEG | Water |
| 1200 | 2000 | 0.044 | 0.044 | No |
|  |  | 0.032 | 0.032 | No |
|  |  | 0.022 | 0.022 | No |
|  |  | 0.011 | 0.011 | Yes |
| 600 | 2000 | 0.017 | 0.017 | Yes |
| 1800 | 2000 | 0.005 | 0.005 | Yes |

TABLE 1-continued

| Initial Molecular Weight | | Concentration (mol/L) | | Solubility in |
|---|---|---|---|---|
| PEI | PEG | PEI | PEG | Water |
| 10000 | 2000 | 0.002 | 0.002 | No |
|  |  | 0.002 | 0.001 | No |
|  |  | 0.0005 | 0.0003 | Yes |

EXAMPLE 2

Figure 2:
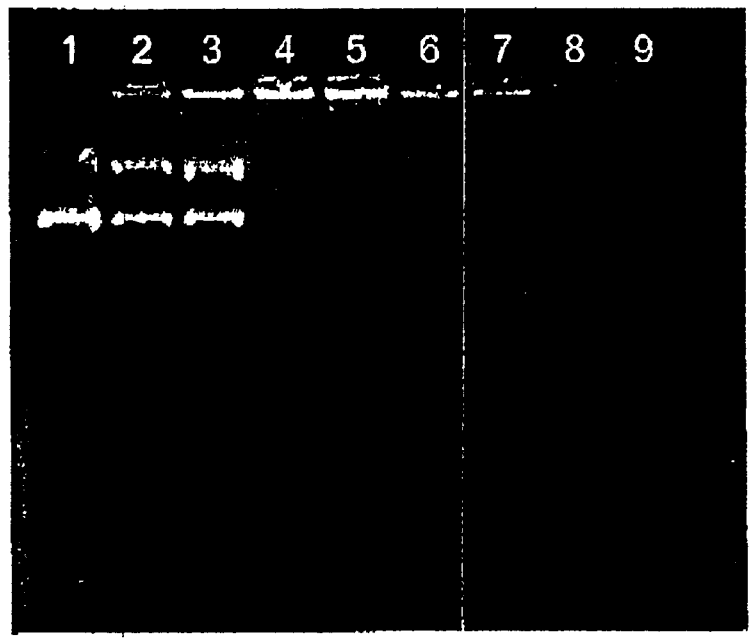
FIG. 2. shows agarose gel electrophoresis of a marker gene pSV-β-gal plasmid and a copolymer comprised of PEI (molecular weight, 1.8K) and PEG (molecular weight, 2.0K) at various copolymer/plasmid weight ratios.

This example illustrates the preparation of a gene delivery composition according to the present invention by mixing a water soluble cationic PEI/PEG copolymer and a pSV-β-gal plasmid DNA (e.g. Promega, Madison, Wis.) in PBS buffer. The PEI/PEG cationic copolymer utilized consisted of PEI (molecular weight, 1,800) and PEG (molecular weight, 2,000) and was prepared as described in Example 1. To study the effect of charge ratio on gene transfer, the plasmid and the water soluble cationic copolymer complexes were prepared at charge ratios of 1, 0.3, 0.6, 0.9, 1.2, 1.5, 1.8, 2.1 and 2, 4. The control composition contained only the 1,800 molecular weight PAI homopolymer instead of the copolymer. Stable complexes were formed with the copolymer and the aqueous plasmid DNA solution based on the fact that no precipitation or aggregation was observed at wide concentration ranges of the complexes in the PBS buffer. The complex formation of the plasmid DNA and the cationic copolymer was tested by agarose gel electrophoresis and the results are shown in FIG. 2. As depicted in FIG. 2, complete neutralization was achieved at the weight ratios of pSV-β-gal plasmid/copolymers from 0.9 to 1.2.

EXAMPLE 3

In this example, compositions comprising pSV-β-gal plasmid DNA and the copolymers of PEI (molecular weight: 1,800) and PEG (molecular weight:2,000) synthesized as in the Example 1 in a weight ratio between 1:7 and 1:16 were prepared and tested for the in vitro delivery and expression of pSV-β-gal plasmid DNA in the 293T cell line. The plasmid pSV-β-gal (EMBL accession no. X65335) is a positive control vector for monitoring transfection efficiencies of mammalian cells. Cell extracts of transfected cells can be measured directly for β-galactosidase activity by a spectrophotometric assay.

In vitro transfection of the 293T cells was performed in 6-well plates seeded at a cell density of $2.25 \times 10^5$ cells/well 24 hours prior to the addition of transfection compositions. The copolymer pSV-β-gal composition (400 μL) was added to cells in the absence of 10% fetal bovine serum. Serum-free transfection mixtures were incubated for 4 hours, followed by supplementation with fetal bovine serum to a level of 10%. Cells were incubated for 40 to 48 hours in an incubator at 37° C. in 5% $CO_2$, the cells were then lysed by addition of Promega Reporter Lysis Buffer (cat. No. E3971). The β-galactosidase activity in the transfected cell lysates were measured by the absorbance at 420 nm.

Figure 3:
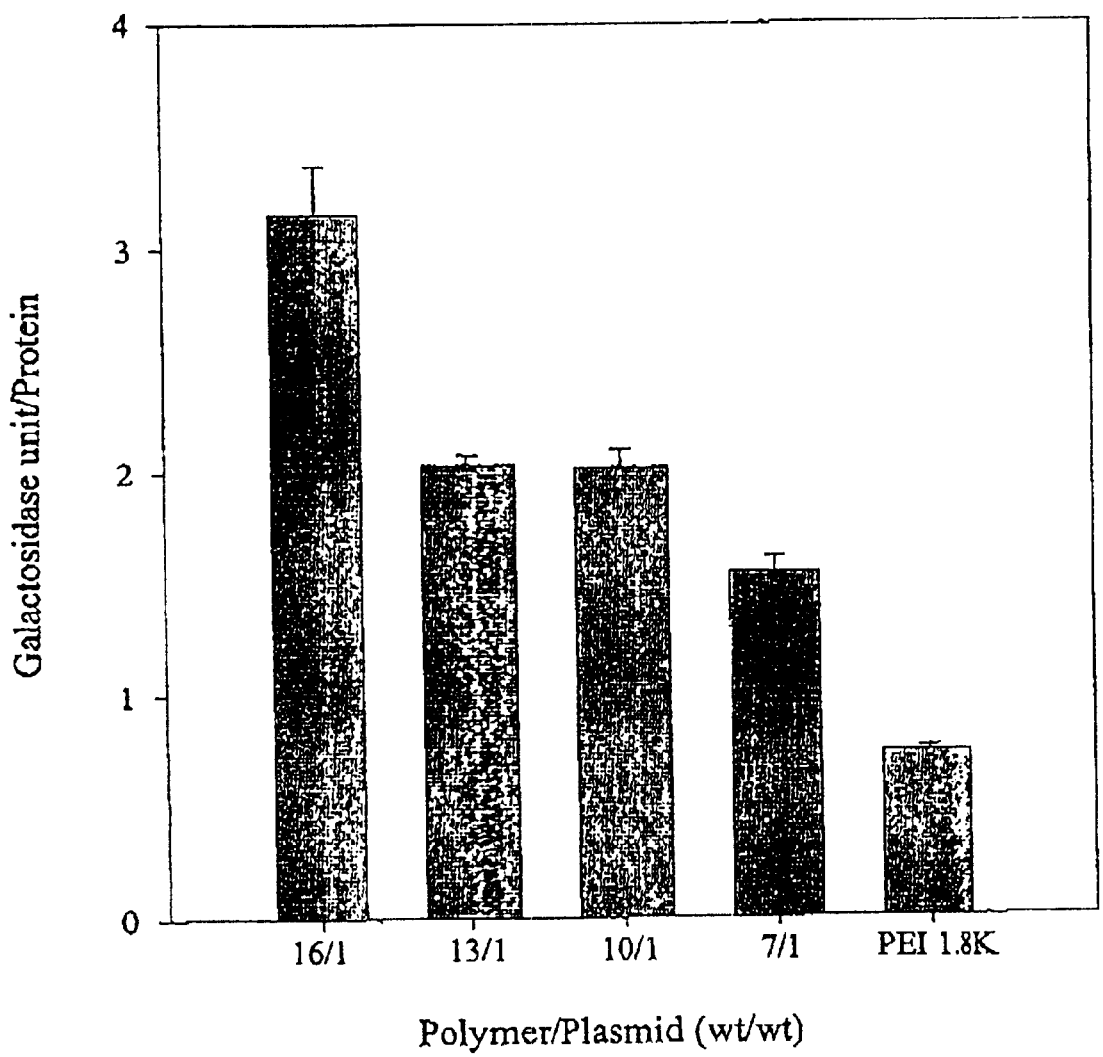
FIG. 3 shows the β-galactosidase activity of lysates of 293T cells transformed with pSV-β-gal plasmids and a copolymer comprised of PEI (molecular weight, 1.8K) and PEG (molecular weight, 2.0K) at various copolymer/plasmid ratios.

FIG. 3 shows the relative β-galactosidase activity of the composition according to the present invention as compared to a PEI control with a molecular weight of 1,800. The transfection efficiency, as measured by β-galactosidase activity of transfected cell extracts, was high and increased as the weight ratio of the copolymer to the plasmid was raised.

EXAMPLE 4

This example illustrates the cytotoxicity of copolymers of the present invention as compared to a BPS buffer control and a 25K PEI polymer, which is the PEI polymer most commonly used for gene delivery application. As shown in Example 1 water soluble PEI/PEG copolymers were prepared having the following molecular weights PEI (mw 600)/PEG(mw 2,000); PEI(mw 1,200)/PEG(mw 2,000) and PEI(mw 1,800)/PEG(mw 2,000). These PEI/PEG complexes, along with the control and the 25,000 PEI polymer were tested for cytotoxicity, using a MTT assay in 293T cells, over the stated range of charge ratios. MTT colorimetric assay as originally described by T. Mosmann, Rapid Colorimetric Assay for Cellular Growth and Survival: Application to Proliferation and Cytotoxicity Assays, 65 J. Immunol. Methods 55–63 (1983), hereby incorporated by reference.

293T cells were grown and maintained in DMEM medium supplemented with 10% fetal bovine serum (FBS), at 37° C. and humidified 5% $CO_2$.

293T cells were seeded at a cell density of $4.5 \times 10^4$ cells/well in a 24-well plates and incubated for 24 hours. The referenced PEI/PEG copolymers and PEI polymer at (20 µg/ml) were added to a cell and incubated for 4 hours at 37° C. in 5% $CO_2$. At the end of the transfection experiment, the transfection mixture was replaced with 500 µL of fresh DMEM medium without serum. 120 µL of 2 mg/ml MTT solution in PBS buffer was added. Plates were incubated for additional 4 hours at 37° C. MTT containing medium was removed and 750 µL of DMSO was added to dissolve the formazan crystal formed by live cells.

Absorbance was measured at 570 nm. The cell viability (%) was calculated according to the following equation;

$$\text{Cell viability (\%)} = (OD_{570(sample)}/OD_{570(control)}) \times 100$$

where $OD_{570(sample)}$ represents the measurement from the wells treated with PEI/PEG copolymers or PEI polymer and $OD_{570(control)}$ from the wells treated with PBS buffer only.

Figure 4:
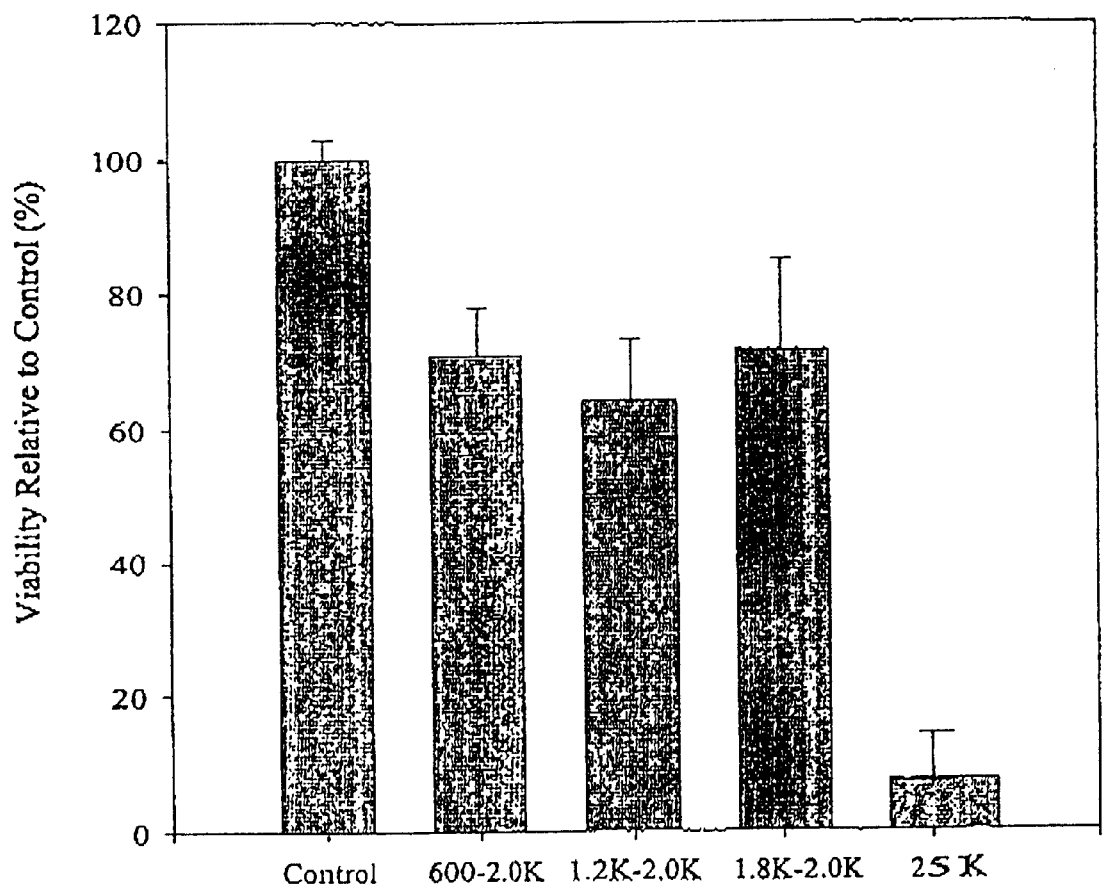
FIG. 4 shows the cytotoxic effect of the copolymers of the present invention on 293T cells.

Decreased cytotoxicity of the present copolymers is confirmed in FIG. 4 showing that cell viability over 60% was obtained for the all the copolymers comprised of initial PEIs with different molecular weights, while that of PEI with a molecular weight of 25K, which is most commonly used in gene therapeutical application, was less than 10%.

An important feature of the PEI/PEG cationic copolymer of the present invention is its relatively low toxicity towards the cells at concentrations required for optimal transfection, for cytotoxicity is one of the major barriers in the application of PAIs as illustrated by this example. The toxicity of some of the commercially available synthetic cationic polymers, such as PAIs, has been attributed to their non-natural, non-biodegradable nature. The results suggest that the biodegradability of the PAI/PEG copolymer of the present invention results in the low cytotoxicity and improved biocompatibility seen.

Thus, among the various embodiments taught there has been disclosed a composition comprising a novel biodegradable cationic copolymer of PAI and a hydrophilic polymer and method of use thereof for delivering bioactive agents, such as DNA, RNA, oligonucleotides, proteins, peptides, and drugs. It will be readily apparent to those skilled in the art that various changes and modifications of an obvious nature may be made without departing from the spirit of the invention, and all such changes and modifications are considered to fall within the scope of the invention as defined by the appended claims.

We claim:

1. A linear biodegradable cationic multi-block copolymer comprising alternating blocks of poly(alkylenimine)(PAI) and hydrophilic polymers with the end blocks of the copolymer being PAI, wherein said PAI is linked with said hydrophilic polymer by a biodegradable bond and wherein said biodegradable cationic copolymer is free of cross linkages and is synthesized by reacting PAI with hydrophilic polymers having difunctional groups.

2. The linear biodegradable cationic copolymer of claim 1 wherein the molar ratio of the PAI to the hydrophilic polymer is within a range of 0.1:1 to 2:1.

3. The linear biodegradable cationic copolymer of claim 2 further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, $Lewis^x$ and sialyl $Lewis^x$, N-acetyllactosamine, galactose, lactose, and thrombomodulin, fusogenic agents, polymixin B, hemaglutinin HA2, lysosomotrophic agents, and nucleus localization signals (NLS).

4. A linear biodegradable cationic multi-block copolymer comprising alternating blocks of poly(alkylenimine)(PAI) and hydrophilic polymers with the end blocks of the copolymer being PAI, wherein said PAI is linked with said hydrophilic polymer by a biodegradable ester or amide bond, and wherein said biodegradable cationic copolymer is free of cross linkages and is synthesized by reacting PAI with hydrophilic polymers having difunctional groups.

5. The linear biodegradable cationic copolymer of claim 4, wherein the PAI has an average molecular weight of 600 to 100,000 Daltons, the hydrophilic polymer has an average molecular weight of 500 to 20,000 Daltons, and the molar ratio of the PAI to the hydrophilic polymer is within a range of 0.1:1 to 2:1.

6. The linear biodegradable cationic copolymer of claim 4, wherein the PAI has an average molecular weight of 600 to 20,000 Daltons, the hydrophilic polymer has an average molecular weight of 500 to 20,000 Daltons, and the molar ratio of the PAI to the hydrophilic polymer is within a range of 0.1:1 to 2:1.

7. The linear biodegradable cationic copolymer of claim 4 further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, $Lewis^x$ and sialyl $Lewis^x$, N-acetyllactosamine, galactose, lactose, and thrombomodulin, fusogenic agents, polymixin B, hemaglutinin HA2, lysosomotrophic agents, and nucleus localization signals (NLS).

8. A linear biodegradable cationic multi-block copolymer comprising alternating blocks of poly(ethylenimine)(PEI) and hydrophilic polymers with the end blocks of the copolymer being PEI, wherein said PEI is linked with said hydrophilic polymer by a biodegradable ester or amide bond, and wherein said biodegradable cationic copolymer is free of cross linkages and is synthesized by reacting PEI with hydrophilic polymers having difunctional groups.

9. The linear biodegradable cationic copolymer of claim 8, wherein the PEI has an average molecular weight of 600 to 100,000 Daltons, the hydrophilic polymer has an average molecular weight of 500 to 20,000 Daltons, and the molar ratio of the PEI to the hydrophilic polymer is within a range of 0.1:1 to 2:1.

10. The linear biodegradable cationic copolymer of claim 8, wherein the PEI has an average molecular weight of 600 to 20,000 Daltons, the hydrophilic polymer has an average molecular weight of 500 to 20,000 Daltons, and the molar ratio of the PEI to the hydrophilic polymer is within a range of 0.1:1 to 2:1.

11. The linear biodegradable cationic copolymer of claim 8, further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, and thrombomodulin, fusogenic agents, polymixin B, hemaglutinin HA2, lysosomotrophic agents, and nucleus localization signals (NLS).

12. A linear biodegradable cationic multi-block copolymer comprising alternating blocks of poly(ethylenimine) (PAI) and hydrophilic polymers which are selected from the group consisting of polyethylene glycol (PEG), polypropylene glycol, poloxamers, poly(acrylic acid), poly(styrene sulfonate), carboxymethylcellulose, poly(vinyl alcohol), polyvinylpyrrolidone, alpha-substituted poly(oxyalkyl) glycols and copolymers of poly(oxyalkyl) glycol, with the end blocks of the block copolymer being PAI, wherein said PAI is linked with said hydrophilic polymer by a biodegradable ester or amide bond and wherein said biodegradable cationic copolymer is free of cross linkages and is synthesized by reacting PAI with hydrophilic polymers having difunctional groups.

13. The linear biodegradable cationic copolymer of claim 12, wherein the PAI has an average molecular weight of 600 to 100,000 Daltons, the hydrophilic polymer has an average molecular weight of 500 to 20,000 Daltons, and the molar ratio of the PAI to the hydrophilic polymer is within a range of 0.1:1 to 2:1.

14. The linear biodegradable cationic copolymer of claim 12, wherein the PAI has an average molecular weight of 600 to 20,000 Daltons, the hydrophilic polymer has an average molecular weight of 500 to 20,000 Daltons, and the molar ratio of the PEI to the hydrophilic polymer is within a range of 0.1:1 to 2:1.

15. The linear biodegradable cationic copolymer of claim 12, further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, and thrombomodulin, fusogenic agents, polymixin B, hemaglutinin HA2, lysosomotrophic agents, and nucleus localization signals (NLS).

16. A linear biodegradable cationic multi-block copolymer comprising alternating blocks of poly(ethylenimine) (PEI) and hydrophilic polymers which are selected from the group consisting of polyethylene glycol (PEG), polypropylene glycol, poloxamers, poly(acrylic acid), poly(styrene sulfonate), carboxymethylcellulose, poly(vinyl alcohol) and polyvinylpyrrolidone, with the end blocks of the block copolymer being PEI, wherein said PEI is linked with the hydrophilic polymer by a biodegradable ester or amide bond and wherein said biodegradable cationic copolymer is free of cross linkages and is synthesized by reacting PEI with hydrophilic polymers having difunctional groups.

17. The linear biodegradable cationic copolymer of claim 16, wherein the PEI has an average molecular weight of 600 to 100,000 Daltons, the hydrophilic polymer has an average molecular weight of 500 to 20,000 Daltons, and the molar ratio of the PEI to the hydrophilic polymer is within a range of 0.1:1 to 2:1.

18. The linear biodegradable cationic copolymer of claim 16, wherein the PEI has an average molecular weight of 600 to 20,000 Daltons, the hydrophilic polymer has an average molecular weight of 500 to 20,000 Daltons, and the molar ratio of the PEI to the hydrophilic polymer is within a range of 0.1:1 to 2:1.

19. The linear biodegradable cationic copolymer of claim 16, further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, and thrombomodulin, fusogenic agents, polymixin B, hemaglutinin HA2, lysosomotrophic agents, and nucleus localization signals (NLS).

20. A linear biodegradable cationic multi-block copolymer comprising alternating blocks of poly(ethylenimine) (PAI) and polyethylene glycol (PEG) with the end blocks of the block copolymer being PAI, wherein said PAI is linked with said PEG by a biodegradable ester or amide bond, and wherein said biodegradable cationic copolymer is free of cross linkages and is synthesized by reacting PAI with hydrophilic polymers having difunctional groups.

21. The linear biodegradable cationic copolymer of claim 20, wherein the PAI has an average molecular weight of 600 to 100,000 Daltons, the PEG has an average molecular weight of 500 to 20,000 Daltons, and the molar ratio of the PAI to the PEG is within a range of 0.1:1 to 2:1.

22. The linear biodegradable cationic copolymer of claim 20, wherein the PAI has an average molecular weight of 600 to 20,000 Daltons, the PEG has an average molecular weight of 500 to 20,000 Daltons, and the molar ratio of the PAI to the PEG is within a range of 0.1:1 to 2:1.

23. The linear biodegradable cationic copolymer of claim 20, further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, and thrombomodulin, fusogenic agents, polymixin B, hemaglutinin HA2, lysosomotrophic agents, and nucleus localization signals (NLS).

24. A linear biodegradable cationic multi-block copolymer comprising alternating blocks of poly(ethylenimine) (PEI) and polyethylene glycol (PEG) with the end blocks of the copolymer being PEI, wherein said PEI is linked with the PEG by a biodegradable ester or amide bond, and wherein said biodegradable cationic copolymer is free of cross linkages and is synthesized by reacting PEI with hydrophilic polymers having difunctional groups.

25. The linear biodegradable cationic copolymer of claim 24, wherein the PEI has an average molecular weight of 600 to 100,000 Daltons, the PEG has an average molecular weight of 500 to 20,000 Daltons, and the molar ratio of the PEI to the PEG is within a range of 0.1:1 to 2:1.

26. The linear biodegradable cationic copolymer of claim 24, wherein the PEI has an average molecular weight of 600 to 20,000 Daltons, the PEG has an average molecular weight of 500 to 20,000 Daltons, and the molar ratio of the PEI to the PEG is within a range of 0.1:1 to 2:1.

27. The linear biodegradable cationic copolymer of claim 24, further comprising a targeting moiety selected from the group consisting of transferrin, asialoglycoprotein, antibodies, antibody fragments, low density lipoproteins, interleukins, GM-CSF, G-CSF, M-CSF, stemcell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, and thrombomodulin, fusogenic agents, polymixin B, hemaglutinin HA2, lysosomotrophic agents, and nucleus localization signals (NLS).

* * * * *

UNITED STATES PATENT AND TRADEMARK OFFICE
CERTIFICATE OF CORRECTION

PATENT NO. : 6,652,886 B2
DATED : January 22, 2004
INVENTOR(S) : Cheol Hee Ahn

It is certified that error appears in the above-identified patent and that said Letters Patent is hereby corrected as shown below:

Title page,
Item [75], Inventors, delete "Sung Wan Kim" as a named co-inventor.

Column 15,
Line 18, delete "poly(ethylenimine" and substitute therefor -- poly(alkylenimine --.

Column 16,
Line 22, delete "poly(ethylenimine" and substitute therefor -- poly(alkylenimine --.

Signed and Sealed this

Thirteenth Day of July, 2004

JON W. DUDAS
*Acting Director of the United States Patent and Trademark Office*